(12) United States Patent
Schajer

(10) Patent No.: US 6,859,046 B2
(45) Date of Patent: Feb. 22, 2005

(54) METHOD AND APPARATUS FOR EVALUATING ANISOTROPIC MATERIALS

(75) Inventor: Gary S. Schajer, Vancouver (CA)

(73) Assignee: Precarn Incorporated, Ottawa (CA)

( * ) Notice: Subject to any disclaimer, the term of this patent is extended or adjusted under 35 U.S.C. 154(b) by 13 days.

(21) Appl. No.: 10/157,913

(22) Filed: May 31, 2002

(65) Prior Publication Data

US 2003/0222658 A1 Dec. 4, 2003

(51) Int. Cl.[7] .............................................. G01R 27/32
(52) U.S. Cl. ...................................................... 324/637
(58) Field of Search ................................. 324/639, 637, 324/642, 76.11, 76.21; 73/600, 602, 618, 659, 584

(56) References Cited

U.S. PATENT DOCUMENTS

| 4,500,835 A | 2/1985 | Heikkila |
| 4,514,680 A | 4/1985 | Heikkila et al. |
| 4,941,357 A | 7/1990 | Schajer |
| 5,619,143 A | 4/1997 | Stevens et al. |

OTHER PUBLICATIONS

Built Environment Innovation & Construction Technology, No. 19, New Electronic Timber Grading—by Microwave, Press Release Jun. 8, 2001; Ref: 2001/142.

*Primary Examiner*—N. Le
*Assistant Examiner*—Amy He
(74) *Attorney, Agent, or Firm*—Antony C. Edwards

(57) ABSTRACT

An apparatus for evaluating dielectrically-anisotropic materials including a plurality of microwave transmitters with differing planes of polarization, and a plurality of microwave receivers with differing planes of polarization, wherein each transmitter includes a device for modulating the microwave beam to be transmitted, the transmitters and receivers arranged, relative to a workplace to be measured, so as to cooperate in communication therebetween, and wherein connected to each receiver is a processor to identify the received amplitude and phase of a component of the transmitted microwave beam, and to analyze by Fourier analysis the received signals to identify the principal axes, attenuations and phase shifts of the received microwave beam without requiring the phases of the transmitted microwave beams to be synchronized.

16 Claims, 2 Drawing Sheets ial by measuring its ultrasound speed in several directions. The principal directions are the directions in which the material stiffness is highest and lowest. For wood, these directions correspond to the grain direction, and the direction perpendicular to the grain. A limitation of the method is that only the principal directions are identified, but not the magnitudes of the corresponding material stiffnesses.

METHOD AND APPARATUS FOR EVALUATING ANISOTROPIC MATERIALS

TECHNICAL FIELD

The invention described here is an apparatus for evaluating the physical properties of anisotropic materials. It was originally conceived as an industrial device for sorting lumber, and therefore the descriptions given below are presented in that context. However, it can be seen that the invention can be successfully applied in much more general contexts. Therefore, the descriptions below should be understood to exemplify just one of a wide range of potential uses.

BACKGROUND

When using wood for industrial purposes, it is important to exercise careful quality control to ensure that the material properties are properly matched to the desired end uses. However, wood is a natural material, and can have a wide range of mechanical properties, even within a single species. Consequently, it is important to be able to sort the wood into different grades, each with specific material properties. Such sorting allows the wood resource to be used efficiently and economically.

Typical wood properties of interest include specific gravity, moisture content, grain direction, stiffness and strength. These properties are of industrial importance both individually and in combination. Perhaps the most challenging property to estimate is wood strength. This is because it is controlled in a subtle way by several different wood characteristics. Accurate identification of wood strength is essential when producing lumber that is to be used for structural applications.

The traditional method for estimating wood strength is by visual observation. The process involves human observation of wood features such a knots and grain distortions. Wood strength is then estimated from the observed features using standardized empirical rules. The visual method is subject to several uncertainties and has only modest strength estimation capabilities.

The bending method is the most common mechanical process for estimating wood strength. The procedure involves bending the wood and measuring the force required to produce a given deflection. The bending method gives a better estimate of wood strength than visual grading, but the estimation accuracy is still only moderate. The available accuracy is mainly limited by the coarse resolution of the stiffness measurement. This measurement is typically done over a 4 foot span, while the main strength controlling features, the knots, are only 0.5–2 inches in diameter. Additionally, a bending machine cannot measure the first and last two feet of a board. Bending machines also require intensive maintenance.

X-ray absorption provides a more accurate method of wood strength grading. Schajer describes the method in U.S. Pat. No. 4,941,357 entitled "Method and Apparatus for Estimating the Strength of Wood." The procedure uses X-ray absorption to indicate the gross density of the wood. The method has fine resolution, comparable to, or finer than, the size of the knots. The X-ray measurements extend from end to end of each board, and so all the material is examined. In addition, the measurements are non-contact, thereby minimizing machine maintenance needs.

Recent advances in computing power have enabled more sophisticated mathematical techniques to be used for wood sorting applications. These mathematical techniques can take into account multiple factors that control wood strength and other properties. They combine the effects of these factors to achieve more accurate wood property estimates. For maximum effectiveness, the mathematical techniques need to work with large amounts of measured data. These data should preferably include measurements of several independent wood properties and they should have fine spatial resolution. The X-ray method provides measurements that partially meet this need. They have fine resolution, but however, they indicate only one wood property, bulk density.

The invention described here is a device that is capable of simultaneously providing fine-resolution of up to five independent wood dielectric properties. These dielectric properties can be used to indicate wood mechanical properties. The invention provides the large amount of fine-resolution, multi-property data that are needed to achieve superior wood strength estimates using the sophisticated mathematical techniques. The same measurements and mathematical techniques can be used to estimate other useful wood properties such as moisture content and stiffness.

PRIOR ART

Several microwave-based methods for measuring wood properties have previously been developed. Typical objectives include knot detection, and identification of wood grain direction and moisture content. The various methods involve measuring the changes in a microwave field that are caused by the presence of the wood. These measurements can be done in reflection mode, where the transmitters and receivers are on the same side of the wood specimen. Alternatively, they can be done in transmission mode, where the transmitters and receivers are on opposite sides of the wood specimen. Typical measured quantities include microwave amplitude, phase shift, resonant frequency and Q factor. A common objective in many microwave system designs is the ability to indicate a particular wood property independent of unknown variations in other wood properties.

In U.S. Pat. No. 3,810,005, Bennion et al. describe a device that identifies knots and flaws in wood by comparing the microwave attenuations measured at adjacent locations. The device is designed to identify knots independent of wood moisture content, density and angle. It therefore does not indicate these three wood properties.

In U.S. Pat. No. 4,123,702, Kinanen also describes a device for identifying knots and other flaws in wood. This device monitors the phase change of a microwave beam that transmits through the wood. The device is also designed to be independent of wood moisture content, density and grain angle, and it therefore does not indicate these three wood properties.

In U.S. Pat. No. 4,500,835, Heikkila describes a device for identifying wood grain direction using switchable, orthogonally polarized transmitters and receivers. By comparing the attenuations measured when different combinations of transmitters and receivers are activated, the grain angle of the wood can be identified. The measurement method allows this angle to be identified independent of the moisture content and density of the wood, and the possible presence of knots. A limitation of the measurement method is that it only indicates the size of the grain angle, but not its sign. Thus, grain deviations to the left or to the right cannot be distinguished.

In U.S. Pat. No. 4,087,746, Kanae describes a method for identifying the principal directions of an orthotropic material. It involves measuring the reflection from a microwave beam whose polarization is mechanically rotated. This method is designed for laboratory measurements with individual samples. It is not well suited to on-line industrial measurements.

In U.S. Pat. No. 4,710,700, Osaki describes a method for identifying the principal directions of a paper sample by measuring resonant frequency and Q factor of a paper sample in a resonant cavity. This method is also designed for laboratory measurements with individual samples, and is not well suited to on-line industrial measurements, In U.S. Pat. No. 5,619,143, Stevens et al. describes a device for measuring wood grain angle. The preferred embodiment uses electrically synchronized Faraday rotators to rotate and de-rotate a linearly polarized microwave beam that transmits through the wood sample. In practical applications, the described device requires careful adjustment and calibration to achieve accurate operation. The electrical alignment of the Faraday rotators must be accurately controlled over the entire range of rotation. Variations in transmitted amplitude and phase of the rotator and de-rotator over the range of rotation must also be accounted for if accurate attenuation and phase shift measurements are to be made. Faraday rotators are relatively low-speed devices that are capable of maximum rotation speeds of a few hundreds of Hz. High-speed, high-resolution applications require measurements at some thousands of Hz.

SUMMARY OF THE INVENTION

The invention described here comprises an apparatus for making microwave measurements on an anisotropic material, and a method for processing those measurements to identify the principal directions, attenuations and phase shifts of the material. The apparatus and method are designed to provide a practical way of measuring material properties under industrial conditions, and where high speed, consistent accuracy and simultaneous measurement of several independent material properties are important.

For ease of explanation, the invention is described here in terms of a specific application referring to wood property measurement. It is to be understood that the usefulness of the invention extends beyond this example application, and that it can be applied to measurements on a wide range of anisotropic materials.

The apparatus consists of a microwave source, two or more microwave transmitters with differing planes of polarization, and two or more microwave receivers, also with differing planes of polarization. Connected to each transmitter is a means of modulating the amplitude of the transmitted microwave beam. Connected to each receiver is a means to identify the received amplitude and the phase relative to the transmitted beam. Further connected to the receivers is a means of analyzing the received amplitude and phase outputs to identify the principal direction, attenuations and phase shifts of the received microwave beam.

In general, the transmitters could be separate or coaxial, and the receivers could be separate or coaxial. The transmitters and receivers could be mounted on opposite sides of the wood sample. This would enable a transmission measurement. Alternatively, the transmitters and receivers could be mounted on the same side of the wood sample. This would enable a reflection measurement.

The transmitted microwave beams are modulated in a known way. The corresponding amplitude and phase outputs from the receivers are then analyzed to determine the dielectric properties of the part of the wood sample through which the transmitted beams passed. It is possible to modulate the transmitted microwave beams and to analyze the received beams using digital methods. In the digital method, a digital device such as a computer provides the modulation signals using a digital-to-analog interface. The received amplitude and phase shift outputs are read using an analog-to-digital interface. Digital control of the modulation signals and analysis of the various outputs allows great flexibility in the operation of the system. Mathematical procedures can be used on the measured data to enhance accuracy and to minimize the effects of measurement errors. Digital control also facilitates interface with other industrial devices, which are likely also to be digital.

The method for using the invention involves first taking reference readings of the amplitude and phase shift outputs. For a transmission type measurement, this requires a clear transmission path between the transmitters and receivers, with no wood present. For a reflection type measurement, this requires insertion of a metal reflector in place of the wood. The reference readings are taken as the transmitted beams are modulated in a specified way. This measurement defines the reference amplitudes and phases. Subsequent amplitude and phase measurements with wood in place are then evaluated relative to the reference measurements. This procedure makes the microwave system self-calibrating and insensitive to variations in the gain and phase shifts of the various microwave components involved.

In many applications, it is of interest to measure the properties of the wood sample in adjacent locations. This can be done by using an apparatus with individual transmitters and receivers for each location. Another possibility is to have all locations illuminated by the same transmitters, with individual receivers for each measurement location. Yet another possibility is to have individual transmitters for each measurement location, with common receivers. All these possibilities form part of the present invention.

BRIEF DESCRIPTION OF THE DRAWINGS

The preferred embodiment of the invention will be described by reference to the accompanying drawings, in which.

EMBODIMENTS OF THE INVENTION

Figure 1:
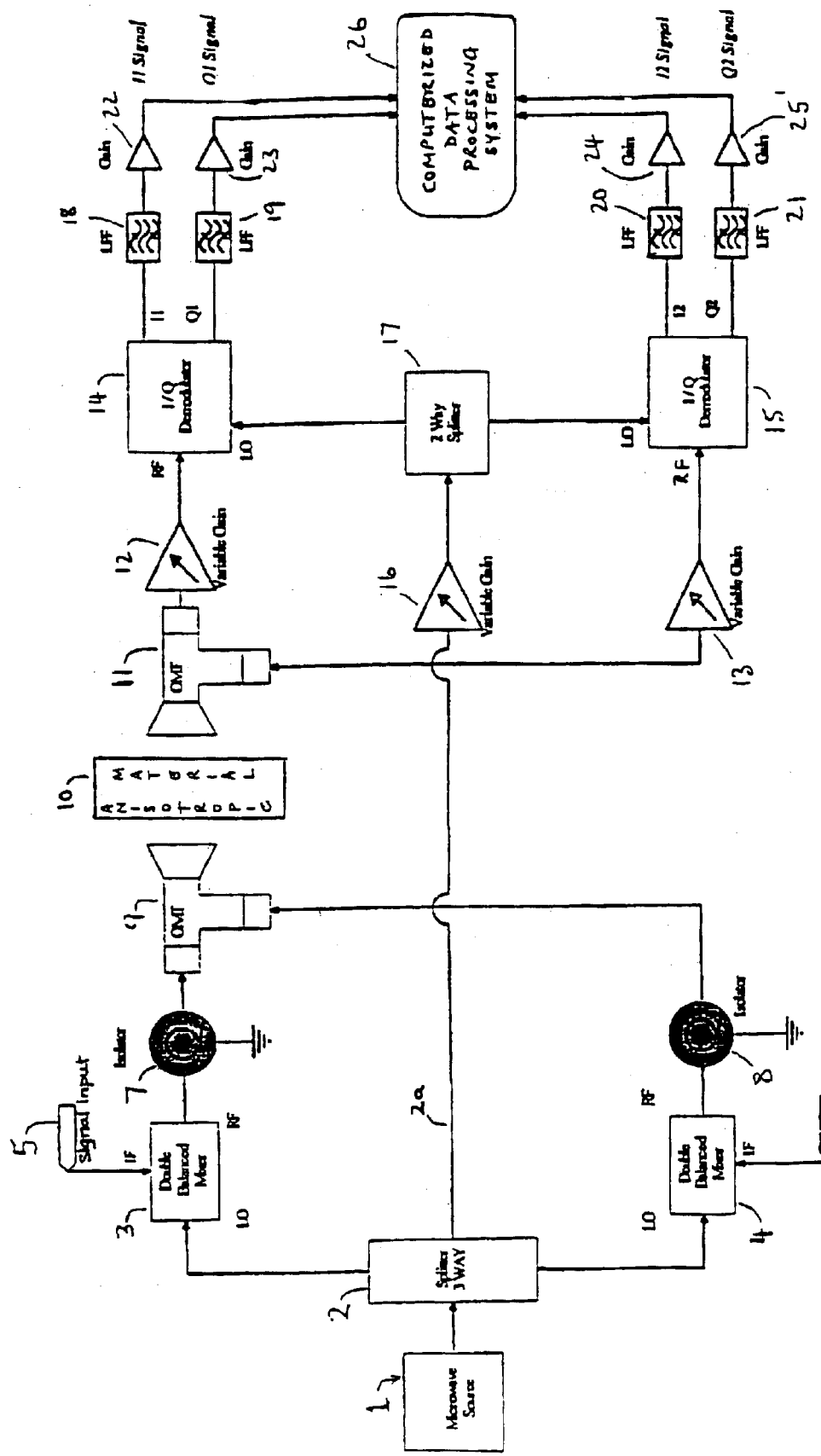
FIG. 1 is a representation of an apparatus embodying the invention that schematically shows a typical arrangement of components.

FIG. 1 shows a schematic diagram of one exemplary embodiment of the invention. A microwave source 1 is connected to a three-way splitter 2. Two branches of the splitter connect to double balanced mixers, 3 and 4, which are modulated by audio frequency signals 5 and 6. The outputs from the double balanced mixers pass through isolators 7 and 8 to an orthomode transducer 9. The orthomode transducer transmits a microwave beam towards and through the wood sample 10. This beam comprises the two signal components with mutually orthogonal planes of polarization. In general, this beam is elliptically polarized. There is no need, nor any effort made, to synchronize the phases of the two orthogonal components. That is, the present invention does not incorporate, nor require a rotator. Were the phases synchronized, then there would be, in effect, a rotating of the beam.

A second orthomode transducer 11 at the other side of the wood receives the orthogonal components of the microwave signal that has passed through the wood. The two orthomode transducers are aligned coaxially and with the same planes of polarization. The received signals pass through amplifiers 12 and 13 to I/Q demodulators 14 and 15. The two I/Q demodulators are referenced to the microwave source 1 through the middle branch of the three-way splitter 2, an amplifier 16 and a two-way splitter 17. The I/Q demodulators each provide outputs corresponding to the components of the received microwave beam components in phase and in quadrature with the microwave source. These outputs pass through low-pass filters 18, 19, 20 and 21, and amplifiers 22, 23, 24 and 25 to a computer system 26. A computer system 26 analyzes the outputs and evaluates their amplitudes and phases. The same computer system provides the audio frequency signals 5 and 6 to the double balanced mixers 3 and 4.

The measurement procedure involves first taking reference readings of I/Q outputs with no wood present between the transmitters and receivers. The two component microwave beams are modulated at audio frequencies using sinusoidal inputs, and with a 90° phase difference between them. The I/Q outputs are measured at least four times at equal time intervals within one cycle of the audio frequency modulation. Measuring the I/Q outputs more than four times over one modulation cycle is desirable because this practice reduces the effects of random measurement errors. Measurements over multiple modulation cycles can also be helpful.

Subsequent similar measurements of the I/Q outputs with wood in place are then evaluated by the computer system. The computer system compares the new measurements with the reference measurements, and uses a mathematical algorithm to evaluate the principal direction and the principal attenuations and phase shifts. These principal quantities correspond to the wood grain direction and the attenuations and phase shifts parallel and perpendicular to the wood grain. The double-measurement procedure without and with wood makes the microwave system self-calibrating and eliminates the need for sensitive adjustment or control of the transmitted beam amplitudes or phases.

Figure 2:
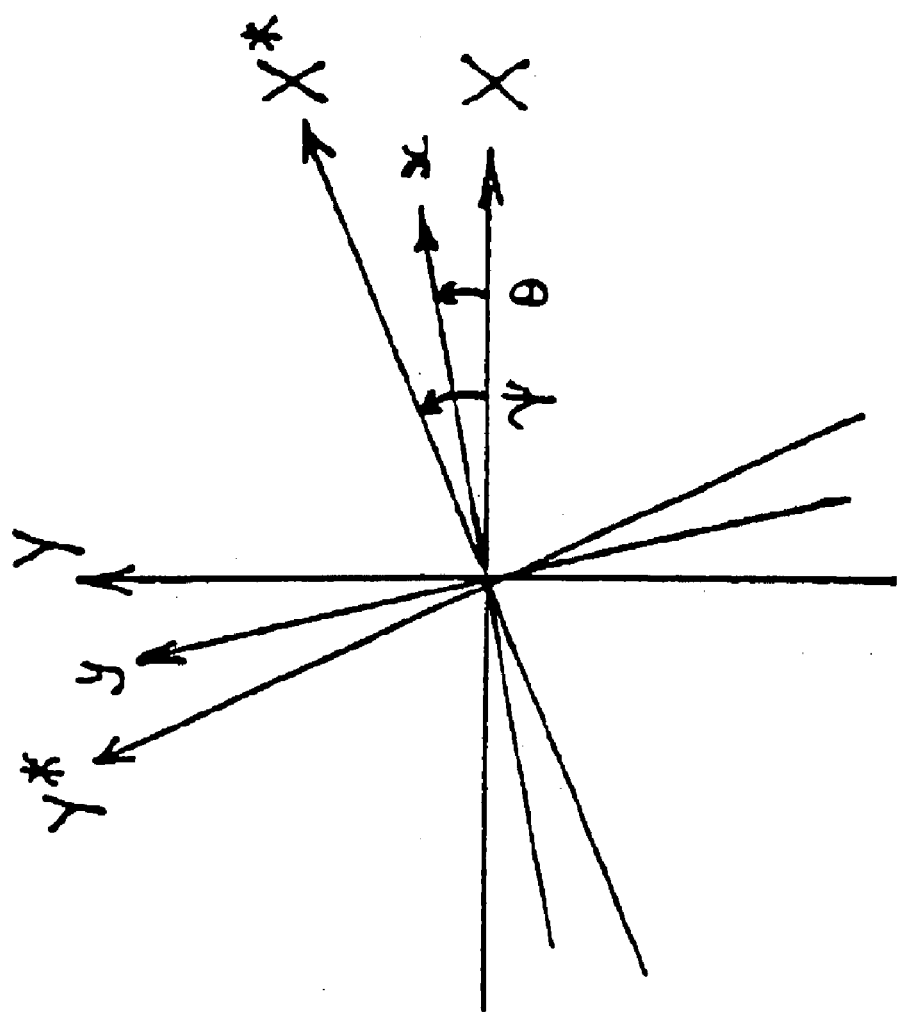
FIG. 2 shows the relationships among the axial directions of the orthogonal transmitters and receivers and the wood grain direction.

FIG. 2 shows three sets of concentric orthogonal axes. Axes X and Y lie in the polarization directions of the receiving orthomode transducer 11 in FIG. 1. Axes X* and Y* lie in the polarization directions of the transmitting orthomode transducer 9. Axes x and y lie in the directions parallel and perpendicular to the grain of the wood sample 10. Angle θ is the wood grain angle measured from the receiver axes, and angle ψ is the misalignment angle between the transmitter and receiver axes.

When a microwave beam transmits through an anisotropic material such as wood, attenuation and phase change of the beam occurs. These effects can be characterized by two constants u and v representing the complex attenuation of the components of the microwave beam that are parallel and perpendicular to the wood grain. In an Argand diagram, the magnitudes of u and v represent the microwave attenuation parallel and perpendicular to the wood grain. The angles of u and v represent the corresponding phase changes.

Let A and B represent the complex amplitudes of the transmitted microwave beam components in directions X*, Y*. In an Argand diagram, the magnitudes and angles of these two quantities represent the microwave beam amplitudes and phases in the two orthogonal directions. The computer system 26 in FIG. 1 provides signals 5 and 6 to the double balanced mixers 3 and 4, thereby modulating the transmitted beam from the orthomode transducer 9. The preferred modulation is periodic, with the modulation phases of A and B differing by 90°.

With sinusoidal modulation, the transmitted amplitudes are A cos ωt and B sin ωt, where ω is the frequency. When no wood is present, the received microwave signals are:

$$D_X = A \cos \omega t \cos \psi - B \sin \omega t \sin \psi \quad (1)$$

$$D_Y = A \cos \omega t \sin \psi + B \sin \omega t \cos \psi \quad (2)$$

The measured outputs from amplifiers 22, 23, 24, 25 attached to the I/Q demodulators 14 and 15 in FIG. 1 correspond to the real and imaginary parts of the complex quantities $D_X$ and $D_Y$. The corresponding transmitted amplitudes A and B can be determined by Fourier analysis of the $D_X$ and $D_Y$ measurements over at least one modulation cycle. The procedure involves numerically evaluating the following quantities.

$$C_X = \frac{\omega}{2\pi} \int_0^{2\pi/\omega} D_X \cos \omega t \, dt \quad C_Y = \frac{\omega}{2\pi} \int_0^{2\pi/\omega} D_Y \cos \omega t \, dt \quad (3)(4)$$

$$S_X = \frac{\omega}{2\pi} \int_0^{2\pi/\omega} D_X \sin \omega t \, dt \quad S_Y = \frac{\omega}{2\pi} \int_0^{2\pi/\omega} D_Y \sin \omega t \, dt \quad (5)(6)$$

$$\tan\psi = \frac{C_Y - S_X}{C_X + S_Y} \text{ or } \frac{C_Y + S_X}{C_X - S_Y} \quad A = \frac{2C_X}{\cos\psi} \quad B = \frac{2S_Y}{\cos\psi} \quad (7)(8)(9)$$

When a wood sample is present, new measurements of $D_X$ and $D_Y$ are taken and new values of the quantities $C_X$, $C_Y$, $S_X$, $S_Y$ are evaluated using equations (3)–(6). The complex attenuations are then calculated using:

$$p = \frac{\frac{C_X}{A} + \frac{S_Y}{B}}{\cos\psi} \quad q = \frac{C_X}{A} - \frac{S_Y}{B} \quad r = -\frac{C_Y}{A} - \frac{S_X}{B} \quad (10)(11)(12)$$

$$\theta = \tfrac{1}{2}(\psi - \arctan(r/q)) \quad (13)$$

$$u, v = p \pm \sqrt{q^2 + r^2} \quad (14)$$

Equations (3) onwards uniquely determine the grain angle θ within the range −90° to 90° and the principal phase shifts within a 360° range.

In practice, the complex attenuations u and v determined from equation (14) are distorted by the effects of microwave reflection and refraction. These effects can be reduced by careful physical design, for example using sloping surfaces and microwave absorbers. The remaining distortions of the indicated attenuations will be consistent, and can be accounted for in the relationships used to identify wood properties from the indicated attenuations. Wood moisture content and specific gravity can be determined from statistical correlations based on the indicated principal attenuations and phase changes. Such evaluations of wood moisture content and specific gravity from principal attenuations and phase changes do not fall within the scope of the present invention.

A person skilled in the art can understand that the present invention can be realized in variant ways that differ from the specific descriptions given herein, and yet still remain within the spirit and scope of the invention. It is therefore to be understood that this invention includes all such variations that fall within its spirit and scope.

What is claimed is:

1. An apparatus for evaluating dielectrically-anisotropic materials comprising:

at least two microwave transmitters, said microwave transmitters having at least three planes of polarization, each transmitter of said microwave transmitters for transmitting a microwave beam of the same frequency, where there is no specific attempt to achieve a rotating plane polarized microwave beam through phase synchronization of the transmitted beam, and at least two microwave receivers having at least three planes of polarization, wherein maid each transmitter of said microwave transmitters includes a means of modulating the microwave beam to be transmitted, wherein said microwave transmitters and said microwave receivers are arranged, relative to a workplace to be measured so as to cooperate in microwave communication therebetween and so as to irradiate the workpiece with the transmitted microwave beam, and wherein connected to each receiver of said microwave receivers is a means to identify the received amplitude and phase of a component of said transmitted microwave beam, and wherein connected to said each receiver is a means for analyzing by Fourier analysis received signals of said transmitted microwave beam to identify principal axes, attenuations and phase shifts of said received signals.

2. The apparatus of claim 1 wherein said microwave transmitters comprise two transmitters having orthogonal planes of polarization, and wherein said microwave receivers comprise two receivers having orthogonal planes of polarization.

3. The apparatus of claim 1 wherein said plurality of microwave transmitters are modulated sinusoidally.

4. The apparatus of claim 1 wherein said transmitters are separate, and said receivers are separate.

5. The apparatus of claim 1 wherein said transmitters axe coaxial, and said receivers are coaxial.

6. The apparatus of claim 1 wherein said transmitters and receivers are located on the opposite sides of the material to be evaluated.

7. The apparatus of claim 1 wherein said transmitters and receivers are located on the same side of the material to be evaluated.

8. In an apparatus for evaluating dielectrically-anisotropic materials which includes a plurality of microwave transmitter transmitting microwave radiation of the same frequency but of no specific phase relationship, having at least three planes of polarization and corresponding phases, and a plurality of microwave receivers having at least three planes of polarization, a method of evaluating dielectrically-anisotropic materials comprising the steps of:

(a) for each transmitter of said plurality of microwave transmitters, modulating the microwave beam to be transmitted, (b) arranging said transmitters and each receiver of said plurality of microwave receivers relative to a workpiece to be measured so as to cooperate in microwave communication between said transmitters and receivers and so as to irradiate the workpiece with the transmitted microwave beam, (c) making no specific attempt to achieve a rotating plane-polarized microwave beam through phase synchronization of the transmitters, (d) for each said receiver, identifying the received amplitude and phase of a component of the transmitted microwave beam, (e) for each said receiver, analyzing by Fourier analysis the received signals to identify the principal axes, attenuation, and phase shifts of the received microwave beam.

9. The method of claim 8 wherein said plurality of microwave transmitters comprise two transmitters having orthogonal planes of polarization, and wherein said plurality of microwave receivers comprise two receivers, said method further comprising the step of orthogonally orienting planes of polarization of said transmitters and receivers, and wherein said step of modulating a transmitted microwave beam includes modulating a transmitted amplitude of a transmitted microwave beam.

10. The method of claim 8 wherein said modulation is sinusoidal modulation.

11. The method of claim 8 wherein adjacent locations in an anisotropic material are evaluated concurrently by using separate transmitters and receivers for each measurement location.

12. The method of claim 8 wherein adjacent locations in an anisotropic material are evaluated concurrently by using common transmitters sad separate receivers for each measurement location.

13. The method of claim 8 wherein adjacent locations in an anisotropic material are evaluated concurrently by using common receivers and separate transmitters for each measurement location.

14. The method of claim 8 where the workpiece and said apparatus move relative to one another.

15. The method of claim 8 where received amplitude and phase signals are digitized, and the principal axes, attenuations and phase shifts of a received microwave beam are determined by digital signal processing techniques.

16. An apparatus for evaluating dielectrically-anisotropic materials comprising a plurality of microwave transmitters, the plurality of microwave transmitters having differing planes of polarization, each transmitter of the plurality of microwave transmitters for transmitting a microwave beam, and a plurality of microwave receivers having differing planes of polarization, wherein each transmitter of the plurality of microwave transmitters includes a means of modulating the transmitted microwave beam, the plurality of microwave transmitters and the plurality of microwave receivers arranged, relative to a workpiece to be measured, so as to cooperate in microwave communication therebetween and so as to irradiate the workpiece with the transmitted microwave beam, and wherein connected to each receiver of the plurality of receivers is a means to identify the received amplitude and phase of a component of microwave beam to be transmitted, and wherein connected to the each receiver is a means for analyzing by Fourier analysis received signals of the transmitted microwave beam to identify principal axes, attenuations and phase shifts of the received signals so that there is no specific attempt to achieve a rotating plane-polarized microwave beam through phase synchronization, wherein fit the Fourier analysis the transmitted amplitudes are A cos ωt and B sin ωt, and wherein ω is the frequency, and wherein $D_X$ and $D_Y$ are complex quantities so that, with no dielectrically-anisotropic material present, $D_X$=A cos ωt cos ψ-B sin ωt sin ψ and $D_Y$=A cos ωt sin ωt cos ψ, wherein the Fourier analysis includes:

(a) determining $D_X$ and $D_Y$ over at least one modulation cycle with no dielectrically-anisotropic material present, (b) numerically evaluating:

$$C_X = \frac{\omega}{2\pi} \int_0^{2\pi/\omega} D_X \cos\omega t \, dt \qquad (i)$$

-continued $$C_Y = \frac{\omega}{2\pi}\int_0^{2\pi/\omega} D_Y\cos\omega t\, dt \quad \text{(ii)}$$

$$S_X = \frac{\omega}{2\pi}\int_0^{2\pi/\omega} D_X\sin\omega t\, dt \quad \text{(iii)}$$

$$S_Y = \frac{\omega}{2\pi}\int_0^{2\pi/\omega} D_Y\sin\omega t\, dt \quad \text{(iv)}$$

$$\tan\psi = \frac{C_Y - S_X}{C_X + S_Y} \text{ or } \frac{C_Y + S_X}{C_X - S_Y} \quad \text{(v)}$$

$$A = \frac{2C_X}{\cos\psi} \quad \text{(vi)}$$

$$B = \frac{2S_Y}{\cos\psi} \quad \text{(vii)}$$

(c) re-determining $D_X$ and $D_Y$ and re-evaluating $C_X$, $C_Y$, $S_X$, $S_Y$ with dielectrically anisotropic material present, (d) calculating the complex attenuations:

$$p = \frac{\frac{C_X}{A} + \frac{S_Y}{B}}{\cos\psi} \quad \text{(i)}$$

$$q = \frac{C_X}{A} - \frac{S_Y}{B} \quad \text{(ii)}$$

$$r = -\frac{C_Y}{A} - \frac{S_X}{B} \quad \text{(iii)}$$

$$\theta = \tfrac{1}{2}(\psi - \arctan(r/q)) \quad (13)$$

$$u, v = p \pm \sqrt{q^2 + r^2}. \quad (14)$$

* * * * *